United States Patent
Izuka et al.

(10) Patent No.: US 10,241,048 B2
(45) Date of Patent: Mar. 26, 2019

(54) BLOOD ANALYZING METHOD AND BLOOD ANALYZER

(71) Applicant: Sysmex Corporation, Kobe-shi, Hyogo (JP)

(72) Inventors: Munehisa Izuka, Kobe (JP); Takuma Watanabe, Kobe (JP)

(73) Assignee: SYSMEX CORPORATION, Kobe-Shi, Hyogo (JP)

( * ) Notice: Subject to any disclaimer, the term of this patent is extended or adjusted under 35 U.S.C. 154(b) by 0 days.

(21) Appl. No.: 14/819,027

(22) Filed: Aug. 5, 2015

(65) Prior Publication Data

US 2016/0041097 A1 Feb. 11, 2016

(30) Foreign Application Priority Data

Aug. 8, 2014 (JP) ................................. 2014-162922

(51) Int. Cl.
*G01N 33/00* (2006.01)
*G01N 31/00* (2006.01)
(Continued)

(52) U.S. Cl.
CPC ..... *G01N 21/6428* (2013.01); *G01N 15/1434* (2013.01); *G01N 21/49* (2013.01);
(Continued)

(58) Field of Classification Search
USPC .............................................. 422/73; 436/10
See application file for complete search history.

(56) References Cited

U.S. PATENT DOCUMENTS 5,585,246 A * 12/1996 Dubrow ............. G01N 15/1468
  435/287.2
8,906,309 B2 * 12/2014 Krockenberger ...... G01N 15/00
  422/73
(Continued)

FOREIGN PATENT DOCUMENTS

CN 101389947 A 3/2009
CN 102016573 A 4/2011
(Continued)

OTHER PUBLICATIONS

CDC: "Comparison of the Plasmodium Species Which Cause Human Malaria", retrieved from the Internet on Nov. 13, 2017 (https://www.cdc.gov/dpdx/resources/pdf/benchaids/malaria/malaria_comparison_p1-2.pdf).*

(Continued)

*Primary Examiner* — Dean Kwak
(74) *Attorney, Agent, or Firm* — Brinks Gilson & Lione (57) ABSTRACT

A blood analyzing method comprises irradiating light on a measurement sample prepared using fluorescent dye so as to produce a difference in fluorescence intensity between reticulocytes and mature red blood cells in a blood sample, detecting scattered light and fluorescent light given off from blood cells in the measurement sample, and obtaining fluorescence data related to the fluorescent light and scattered light data related to the scattered light for each blood cell, determining the possibility of the presence of *plasmodium falciparum* parasites in the blood sample based on the distribution conditions of blood cells in the reticulocyte distribution range based on the scattered light data and the fluorescent light data.

5 Claims, 9 Drawing Sheets

(51) Int. Cl.
*G01N 21/64* (2006.01)
*G01N 33/569* (2006.01)
*G01N 15/14* (2006.01)
*G01N 21/49* (2006.01)
*G01N 33/49* (2006.01)
*G01N 15/00* (2006.01)

(52) U.S. Cl.
CPC ....... *G01N 33/49* (2013.01); *G01N 33/56905* (2013.01); *G01N 2015/0073* (2013.01); *G01N 2015/1486* (2013.01); *G01N 2021/6439* (2013.01); *G01N 2201/06113* (2013.01); *Y02A 50/58* (2018.01)

(56) References Cited

U.S. PATENT DOCUMENTS

| | | | | |
|---|---|---|---|---|
| 2002/0084172 | A1* | 7/2002 | Toms | G01N 15/0227 198/445 |
| 2004/0067575 | A1* | 4/2004 | Hanaoka | G01N 33/56905 435/252.3 |
| 2004/0132196 | A1* | 7/2004 | Mizukami | G01N 15/1456 436/63 |
| 2005/0221396 | A1* | 10/2005 | Simon-Lopez | G01N 33/56905 435/7.22 |
| 2006/0223137 | A1* | 10/2006 | Yoshida | G01N 33/56905 435/34 |
| 2006/0259249 | A1* | 11/2006 | Sampath | G06F 19/24 702/20 |
| 2007/0020721 | A1* | 1/2007 | Yoshida | G01N 15/1459 435/34 |
| 2011/0136152 | A1* | 6/2011 | Lin | G01N 15/1475 435/7.25 |
| 2012/0157160 | A1* | 6/2012 | Ozcan | G01N 21/6458 455/556.1 |
| 2014/0120530 | A1* | 5/2014 | Otsuka | G01N 21/49 435/6.1 |
| 2017/0059486 | A1* | 3/2017 | Suzuki | G01N 21/47 |

FOREIGN PATENT DOCUMENTS

| | | |
|---|---|---|
| CN | 103091286 A | 5/2013 |
| EP | 1 406 088 A2 | 4/2004 |
| EP | 1 715 345 A1 | 10/2006 |
| EP | 1 746 407 A2 | 1/2007 |
| JP | 2006-101708 A | 4/2006 |
| JP | 2006-304774 A | 11/2006 |
| JP | 2007-024844 A | 2/2007 |
| JP | 4659146 B | 3/2011 |
| JP | 2012-168192 A | 9/2012 |
| JP | 2012-233889 A | 11/2012 |
| WO | WO 2013/064078 A1 | 5/2013 |

OTHER PUBLICATIONS

Hobro, A. et al., "Raman Spectroscopic Analysis of Malaria Disease Progression via Blood and Plasma Samples", *Analyst* (*The Royal Society of Chemistry*), vol. 138, No. 14, Jan. 2013, pp. 3927-3933.

* cited by examiner

FIG. 4 (a)  1st measurement, no malaria infection

FIG. 4 (b)  1st measurement, plasmodium vivax

FIG. 5 (a)  2nd measurement, no malaria infection

FIG. 5 (b)  2nd measurement, plasmodium vivax

FIG. 6

FIG. 7 (a)   3rd measurement, no malaria infection

FIG. 7 (b)   3rd measurement, plasmodium falciparum

FIG. 9 (a)

|  |  | Positive | Negative |
|---|---|---|---|
| Visual | Positive | 0 | 23 |
|  | Negative | 0 | 76 |

| Sensitivity | 0.0% |
|---|---|
| Specificity | 100% |
| PPV | —% |
| NPV | 76.8% |

FIG. 9 (b)

|  |  | Positive | Negative |
|---|---|---|---|
| Visual | Positive | 17 | 6 |
|  | Negative | 1 | 75 |

| Sensitivity | 73.9% |
|---|---|
| Specificity | 98.7% |
| PPV | 94.4% |
| NPV | 92.6% |

BLOOD ANALYZING METHOD AND BLOOD ANALYZER

CROSS REFERENCE TO RELATED APPLICATIONS

This application claim priority from prior Japanese Patent Application No. 2014-162922, filed on Aug. 8, 2014, entitled "BLOOD ANALYZING METHOD, BLOOD ANALYZER, AND PROGRAM", the entire contents of which are incorporated herein by reference.

FIELD OF THE INVENTION

The present invention relates to a blood analyzing method for counting blood cells in a blood sample, and blood analyzer.

BACKGROUND

*Plasmodium falciparum, plasmodium vivax, plasmodium ovale*, and *plasmodium milariae* are known types of malaria. Among these, *plasmodium falciparum* malaria is likely to become severe in humans, and those infected require prompt medical treatment. Methods of diagnosing those infected by malaria include, for example, the method described in Japanese laid-open patent No. 2007-24844. In this method, a measurement sample is prepared by adding reagent for lysing red blood cells to a blood sample. Optical information is obtained when the prepared measurement sample is irradiated with light, and the presence or absence of malaria parasites in the measurement sample is determined based on the obtained optical information. In this case, malaria parasites and white blood cells are discriminated using a white blood cell detection scattergram.

Among these four types of malaria, the malaria parasites of *plasmodium falciparum* often form a ring formation in red blood cells. The malaria parasites of the ring formation cannot be detected by the method disclosed in Japanese laid-open patent No. 2007-24844 because the size is smaller than the red blood cells.

SUMMARY OF THE INVENTION

The blood analyzing method of a first aspect of the present invention includes irradiating light on a measurement sample prepared using fluorescent dye so as to produce a difference in fluorescence intensity between reticulocytes and mature red blood cells in a blood sample, detecting scattered light and fluorescent light given off from blood cells in the measurement sample, and obtaining fluorescence data related to the fluorescent light and scattered light data related to the scattered light for each blood cell, and determining the possibility of the presence of *plasmodium falciparum* parasites in the blood sample based on the distribution conditions of blood cells in the reticulocyte distribution range based on the scattered light data and the fluorescent light data.

The blood analyzer of a second aspect of the present invention is provided with a sample preparing part for preparing a measurement sample using a fluorescent dye to produce a difference in fluorescence intensity between mature red blood cells and reticulocytes in a blood sample, a detecting part for detecting scattered light and fluorescent light produced by irradiating light on blood cells in the measurement sample and detecting the scattered light data related to the scattered light and the fluorescent light data related to the fluorescent light for each blood cell, and a controller for determining the possibility of the presence of *plasmodium falciparum* parasites in the blood sample based on distribution conditions of blood cells in the reticulocyte distribution range based on the scattered light data and the fluorescent light data.

The blood analyzer of a third aspect of the present invention is provided with a detecting part for detecting scattered light and fluorescent light produced by irradiating light on blood cells in a measurement sample prepared from a blood sample, and detecting fluorescence data related to the fluorescent light and scattered light data related to the scattered light for each blood cell, and a controller for executing a first measurement for determining the possibility of the presence of at least one among *plasmodium vivax* parasites, *plasmodium ovale* parasites, and *plasmodium malariae* parasites, and a second measurement for determining the possibility of the presence of *plasmodium falciparum* parasites.

The possibility of the presence of *plasmodium falciparum* parasites in a blood sample can be determined by the present invention.

BRIEF DESCRIPTION OF THE DRAWINGS

FIGS. 5(a) and (b) show scattergrams and ranges based on the second measurement of the embodiment.

FIGS. 7(a) and (b) show scattergrams and ranges based on the third measurement of the embodiment.

FIG. 8(a) is a flow chart showing the display process of the embodiment.

FIGS. 8(b) and (c) are schematic views showing the structures of the screens of the embodiment.

DETAILED DESCRIPTION OF THE PREFERRED EMBODIMENTS

Figure 1:
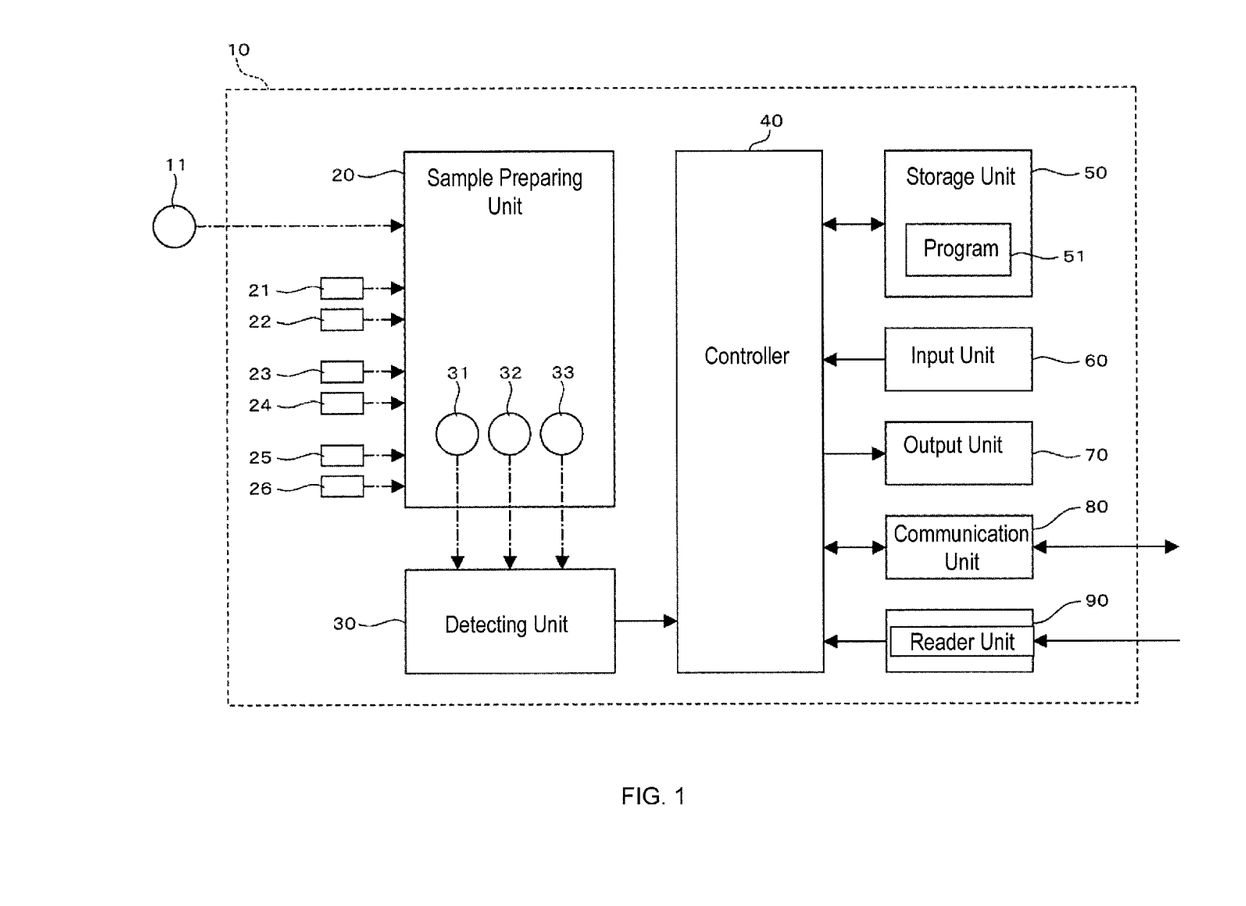
FIG. 1 is a block diagram showing the structure of the blood analyzer of an embodiment.

As shown in FIG. 1, a blood analyzer 10 is provided with a sample preparing unit 20, a detecting unit 30, controller 40, storage unit 50, input unit 60, output unit 70, communication unit 80, and reader unit 90.

The blood analyzer 10 performs a first measurement, second measurement, and third measurement. In the first measurement, blood cells or the like are classified as nucleated red blood cells, basophils, and white blood cells excluding basophils. In the second measurement, blood cells and the like are classified as blood cells of lymphocytes, monocytes, eosinophils, combined neutrophils and basophils. In the third measurement, blood cells are classified as mature red blood cells, reticulocytes, and platelets. The term "red blood cells" is used below to include both reticulocytes and mature red blood cells.

The sample preparing unit 20 receives the blood sample 11 of peripheral blood collected from a patient. A container holding reagents 21 through 26 is connected to the sample preparing unit 20. The sample preparing unit 20 prepares a measurement sample 31 by mixing reagent 21 and 22 with a blood sample 11, prepares a measurement sample 32 by mixing reagent 23 and 24 with a blood sample 11, and prepares a measurement sample 33 by mixing reagents 25 and 26 with a blood sample 11. The measurement samples 31 through 33 are sent to the detecting unit 30 through the flow path.

Reagent 21 contains surfactant to lyse the red blood cells, reagent 22 contains fluorescent dye to produce a difference in fluorescence intensity between white blood cells and nucleated red blood cells in the blood sample 11. For example, Lyzercell (registered trademark) WNR (registered trademark) manufactured by Sysmex Corporation may be used as reagent 21, and, for example, Fluorocell (registered trademark) WNR may be used as reagent 22. Reagent 23 contains surfactant to lyse the red blood cells, reagent 24 contains fluorescent dye to produce a difference in fluorescence intensity among subclasses of white blood cells in the blood sample 11. For example, Lyzercell WNF (registered trademark) manufactured by Sysmex Corporation may be used as reagent 23, and, for example, Fluorocell WDF manufactured by Sysmex Corporation may be used as reagent 24. Reagent 25 is a diluting liquid, and reagent 26 contains fluorescent dye to produce a difference in fluorescence intensity between mature red blood cells and reticulocytes in the blood sample 11. For example, Cellpack (registered trademark) DFL (registered trademark) manufactured by Sysmex Corporation may be used as reagent 25, and, for example, Fluorocell RET (registered trademark) may be used as reagent 26.

Note that reagents 25 and 26 do not lyse red blood cells. Reagents 25 and 26 may be changed within the range of capability of measuring reticulocytes and mature red blood cells without lysing red blood cells. In this case, the phrase "do not lyse red blood cells" includes not damaging red blood cells to promote staining by a small amount of surfactant. Note that a plurality of reagents are used in the preparation of the measurement samples 31 through 33 in the present embodiment. However, the present invention is not limited to this arrangement, and the measurement samples 31 through 33 also may be prepared by mixing a single reagent with the blood sample 11.

The detecting unit 30 irradiates light on the measurements samples 31 through 33, and detects the forward scattered light, side scattered light, and fluorescent light given off from the blood cells in the measurement samples 31 through 33. The detecting unit 30 obtains the forward scattered light data related to the forward scattered light side scattered light data related to the side scattered light, and the fluorescent light data related to the fluorescent light based on each light. The detecting unit 30 outputs these data to the controller 40. The detecting unit 30 is described below referring to FIG. 2.

The controller 40 stores the forward scattered light data, side scattered light data, and fluorescent light data in the storage unit 50. The storage unit 50 holds a pre-stored program 51 which is used for blood cell analysis. The controller 40 executes the program 51 when performing analysis of the blood cells shown below.

The controller 40 performs the respective classifications described above based on the data obtained in the first measurement and the second measurement. The controller 40 also determines the possibility of the presence of types of malaria parasites other than *plasmodium falciparum* in the blood sample 11 based on the data obtained in the first measurement and the second measurement. Types of malaria parasites other than *plasmodium falciparum* are *plasmodium vivax*, *plasmodium ovale*, and *plasmodium malariae*. The types of malaria parasites other than *plasmodium falciparum* are referred to as "other malaria parasites" below. The process of determining the possibility of the presence of other malaria parasites is described below referring to FIG. 3.

The controller 40 performs the classifications described above based on the data obtained in the third measurement. The controller 40 also determines the possibility of the presence of *plasmodium falciparum* parasites in the blood sample 11 based on the data obtained in the third measurement. The process of determining the possibility of the presence of *plasmodium falciparum* parasites is described below referring to FIG. 6.

The controller 40 receives the instructions from the operator through the input unit 60, and displays the blood cell analysis results on the output unit 70. The input unit 60 includes a mouse and keyboard, and the output unit 70 is a display unit. The controller 40 communicates with and external computer and the like through the communication unit 80, and reads external programs through the reader unit 90. The reader unit 90 is an optical drive. The program 51 which is used to analyze blood cells is not limited to being pre-stored in the storage unit 50, and may be stored in the storage unit 50 from an external source through the communication 80 and reader unit 90 prior to blood cell analysis.

Figure 2:
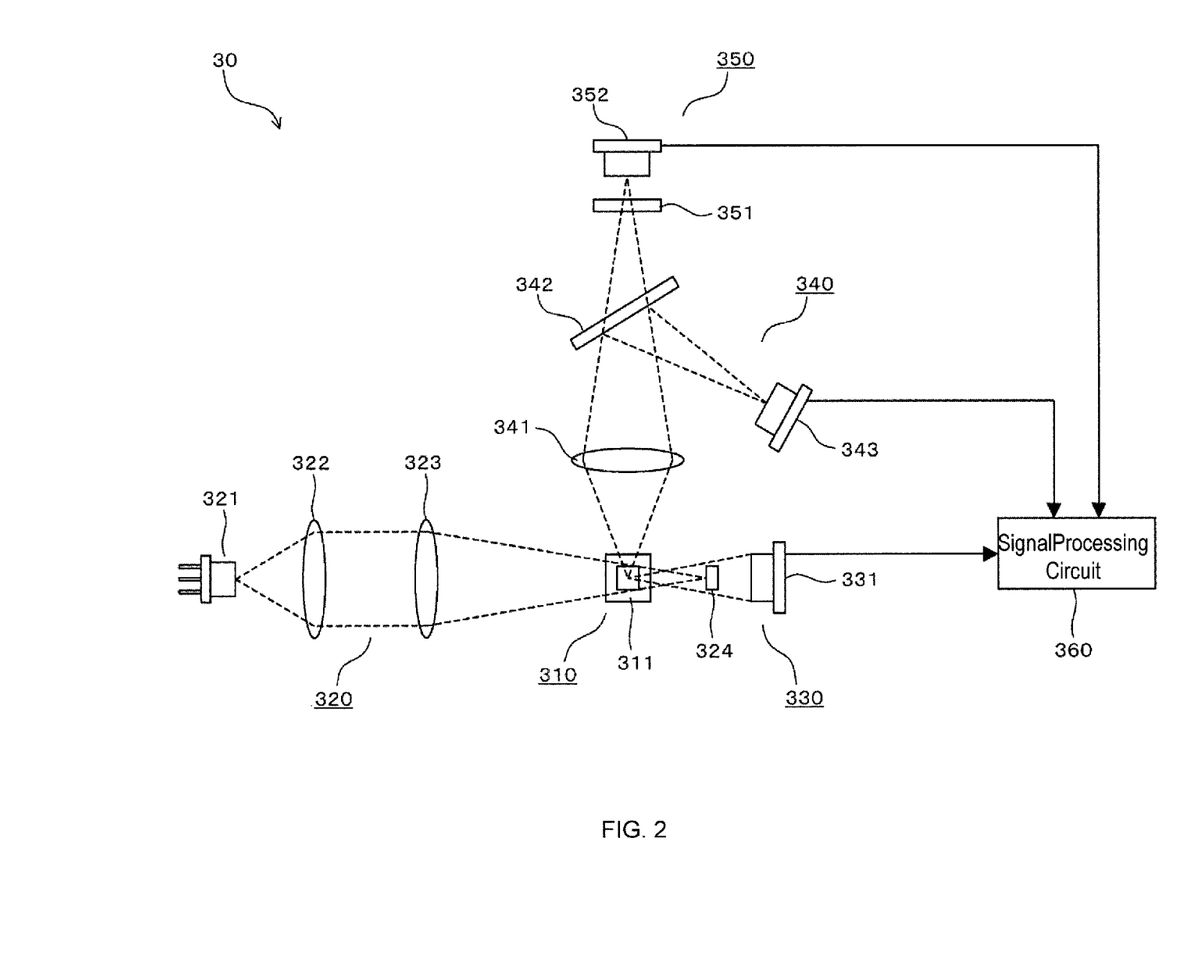
FIG. 2 is a schematic view of the structure of the detecting part of the embodiment.

As shown in FIG. 2, the detecting unit 30 has a sheath flow system 310, a beam spot forming system 320, a forward scattered light receiving system 330, a side scattered light receiving system 340, a fluorescent light receiving system 350, and a signal processing circuit 360.

The sheath flow system 310 has a flow cell 311. The flow cell 311 is configured by a transparent material formed in a tubular shape. The measurement samples 31 through 33 flow within the flow cell 311 encapsulated in a sheath fluid. The particles contained in the measurement samples 31 through 33 pass through the flow cell 311 in single file array.

The beam spot forming system 320 is configured to irradiate light emitted from a light source 321 through a collimator lens 322 and condenser lens 323 onto the measurement samples 31 through 33 flowing through the flow cell 311. The light source 321 is a semiconductor laser, and the light emitted from the light source 321 is laser light in the red color wavelength band. Note that the wavelength of the light emitted from the light source 321 may be suitably modified within a range which allows classification of blood cells as mentioned above.

When the particles contained in the measurement samples 31 through 33 are irradiated by the light, the particles in the measurement sample 31 through 33 give off forward scattered light, side scattered light, and fluorescent light. The forward scattered light reflects information related to the size of the particles, the side scattered light reflects information related to the interior of the particles, and the fluorescent light reflects the degree of staining of the particles. Among the light which irradiates the flow cell 311, the light that has passed through the flow cell 311 without irradiating a particle is blocked by a beam stopper 324.

The forward scattered light receiving system 330 is configured to receive the forward scattered light by a photodetector 331. The photodetector 331 is a photodiode which outputs electrical signals corresponding to the intensity of the received forward scattered light. The side scattered light receiving system 340 is configured to collect the side scattered light by a side collector lens 341, reflect the side scattered light by a dichroic mirror 342, and receive the light by a photodetector 343. The photodetector 343 is a photodiode which outputs electrical signals corresponding to the intensity of the received side scattered light. The fluorescent light receiving system 350 is configured to collect the fluorescent light by the side collecting lens 341, transmit the fluorescent light through the dichroic mirror 342, and pass the fluorescent light through a spectral filter 351, and receive the fluorescent light by a photodetector 352. The photodetector 352 is a photodiode which outputs electrical signals corresponding to the intensity of the received fluorescent light.

The signal processing circuit 360 obtains respective signal waveform information corresponding to the forward scattered light, side scattered light, and fluorescent light by performing predetermined signal processing on the electrical signals output from the photodetectors 331, 343, and 352. The signal processing circuit 360 obtains the peak value of the signal waveform of the respective obtained signal waveforms, and performed A/D conversion of the peak values. In this way the signal processing circuit 360 obtains digital data of the peak values of each signal waveform, that is, forward scattered light data related to the forward scattered light, side scattered light data relative to the side scattered light, and fluorescent light data related to the fluorescent light for each particle contained in the measurement samples 31 through 33. The signal processing circuit 360 outputs the data of each light obtained in this way to the controller 40 shown in FIG. 1.

Note that the optical system of the detecting unit 30 may be suitably changed from the configuration shown in FIG. 2.

The process performed by the blood analyzer 10 is described below referring to the flow chart. When the start instruction is issued by the operator, the blood analyzer 10 sequentially performs a process to aspirate the blood sample 11 and supply the aspirated sample to the sample preparing unit 20, and a process related to the first measurement and second measurement shown in FIG. 3, and performs a process related to the third measurement shown in FIG. 6.

Figure 3:
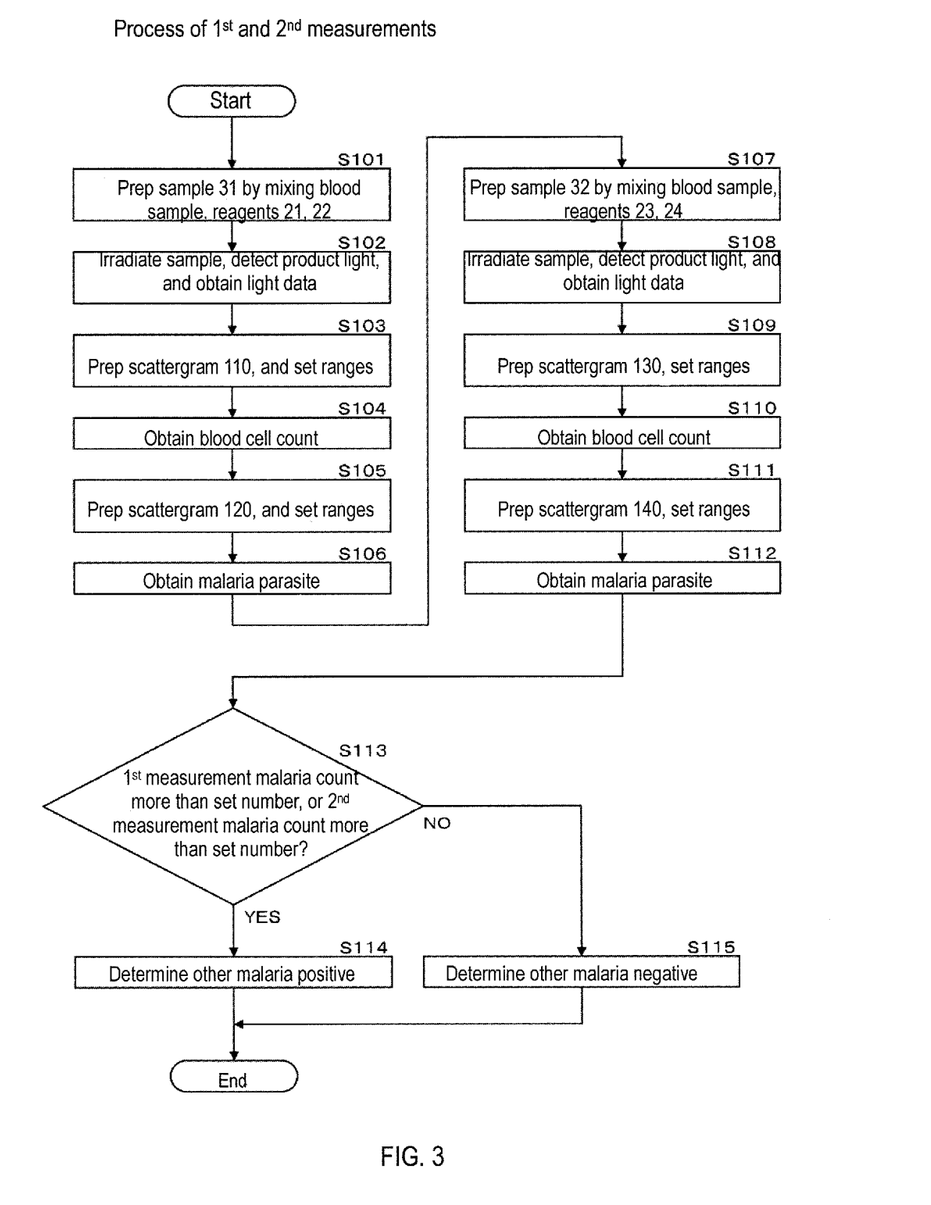
FIG. 3 is a flow chart showing the process related to the first measurement and the second measurement of the embodiment.

As shown in FIG. 3, in step S101 the sample preparing unit 20 prepares the measurement sample 31 by mixing the blood sample 11 and reagents 21 and 22. In the preparation of the measurement sample 31, the red blood cells within the blood sample 11 are lysed by the action of the reagent 21. This time, when malaria parasites are present in the red blood cells, the malaria parasites are released into the liquid. The detecting unit 30 flows the measurement sample 31 through the flow cell 311. In step S102, the detecting unit 30 irradiates light on the measurement sample 31, and the forward scattered light, side scattered light, and fluorescent light are respectively detected by the photodetectors 331, 343, and 352, and the forward scattered light data, side scattered light data, and fluorescent light data are obtained for each particle.

Figure 4A:
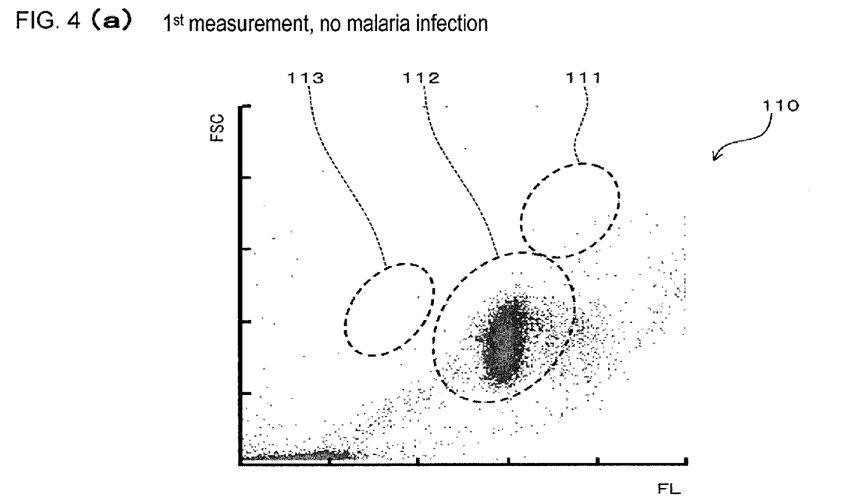
FIGS. 4(a) and (b) show scattergrams and ranges based on the first measurement of the embodiment.

In step S103, the controller 40 prepares a scattergram 110 shown in FIG. 4(a) based on the data obtained in step S102, and sets ranges 111 through 113 on the scattergram 110. The horizontal axis and the vertical axis of the scattergram 110 represent the fluorescent light data and the forward scattered light data, respectively. FIG. 4(a) shows the scattergram 110 based on a blood sample 11 collected from a patient who does not have malaria. The ranges 111 through 113 are respectively ranges which contain basophils, white blood cells excluding basophils, and nucleated red blood cells. The controller 40 classifies the points contained in each range as blood cells corresponding to each of the ranges. In step S104, the controller 40 counts the number of particles included in each range 111 through 113, and obtains the number of basophils, number of white blood cells excluding basophils, and number of nucleated red blood cells, respectively.

Note that in this case the scattergram 110 is prepared and the ranges 111 through 113 are set on the scattergram 110 to obtain the number of particles in the ranges 111 through 113 for the convenience of the description. However, obtaining the number of particles corresponding to the ranges 111 through 113 does not necessarily require the use of graphics or graphs. That is, instead of the processes of steps S103 and S104, particles belonging to a predetermined numerical value range can be extracted by filtering, and the numbers of particles within the ranges 111 through 113 can be obtained by performing data processing to count the number of extracted particles. Similarly, obtaining the number of particles and number of blood cells does not necessarily require the use of graphics or graphs in steps S105 and S106, steps S109 and S110, steps S111 and S112, and steps S203 and S204 of FIG. 6.

Figure 4B:
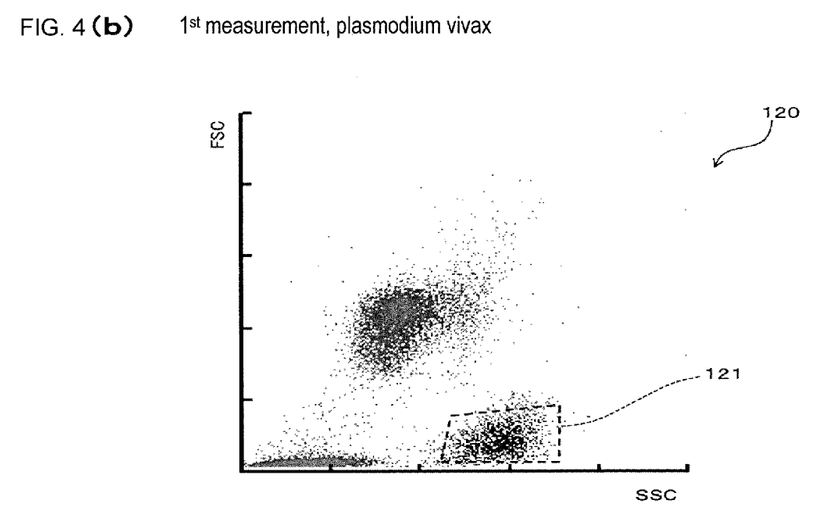

In step S105, the controller 40 prepares a scattergram 120 shown in FIG. 4(b) based on the data obtained in step S102, and sets a range 121 on the scattergram 120. The horizontal axis and the vertical axis of the scattergram 120 represent the side scattered light data and the forward scattered light data, respectively. FIG. 4(b) shows the scattergram 120 based on a blood sample 11 collected from a patient infected with *plasmodium vivax* malaria.

Malaria parasites take the form of a ring-shaped body, mature trophozoite, and schizont body within the red blood cell. Since malaria parasites other than *plasmodium falciparum* often take a form other than ring-shaped body within the red blood cells of peripheral blood, the size of these non-*plasmodium falciparum* parasites is often the same as the size of white blood cells. However, the non-*plasmodium falciparum* parasites can be classified based on the data obtained in the first measurement used to classify white blood cells. Range 121 is a range that is considered to contain other malaria parasites. In step S106, the controller 40 counts the number of particles contained in range 121, and obtains the number of other malaria parasites.

On the other hand, since *plasmodium falciparum* parasites often take the form of a ring-shaped body within red blood cells of peripheral blood, the size of the *plasmodium falciparum* parasite is often several steps smaller than the size of red blood cells. The *plasmodium falciparum* parasite maintains a ring-like form as red blood cells containing the *plasmodium falciparum* parasite are lysed. Accordingly, the *plasmodium falciparum* parasite is difficult to classify since the majority of *plasmodium falciparum* parasites overlap the range of debris in the scattergram 110 even when *plasmodium falciparum* parasite is classified based on the data obtained in the first measurement used to classify white blood cells. In the present embodiment, the possibility of the presence of the *plasmodium falciparum* parasite in the blood sample 11 is determined based on the data obtained by the third measurement which is used to classify reticulocytes. This determination is described below referring to FIG. 6.

In step S107, the sample preparing unit 20 then prepares the measurement sample 32 by mixing the reagents 23 and 24 with the blood sample 11. In the preparation of the measurement sample 32, the red blood cells within the blood sample 11 are lysed by the action of the reagent 23. This time, when malaria parasites are present in the red blood cells, the malaria parasites are released into the liquid. The detecting unit 30 flows the measurement sample 32 through the flow cell 311. In step S108, the detecting unit 30 obtains each of the light data similar to step S102.

Figure 5:
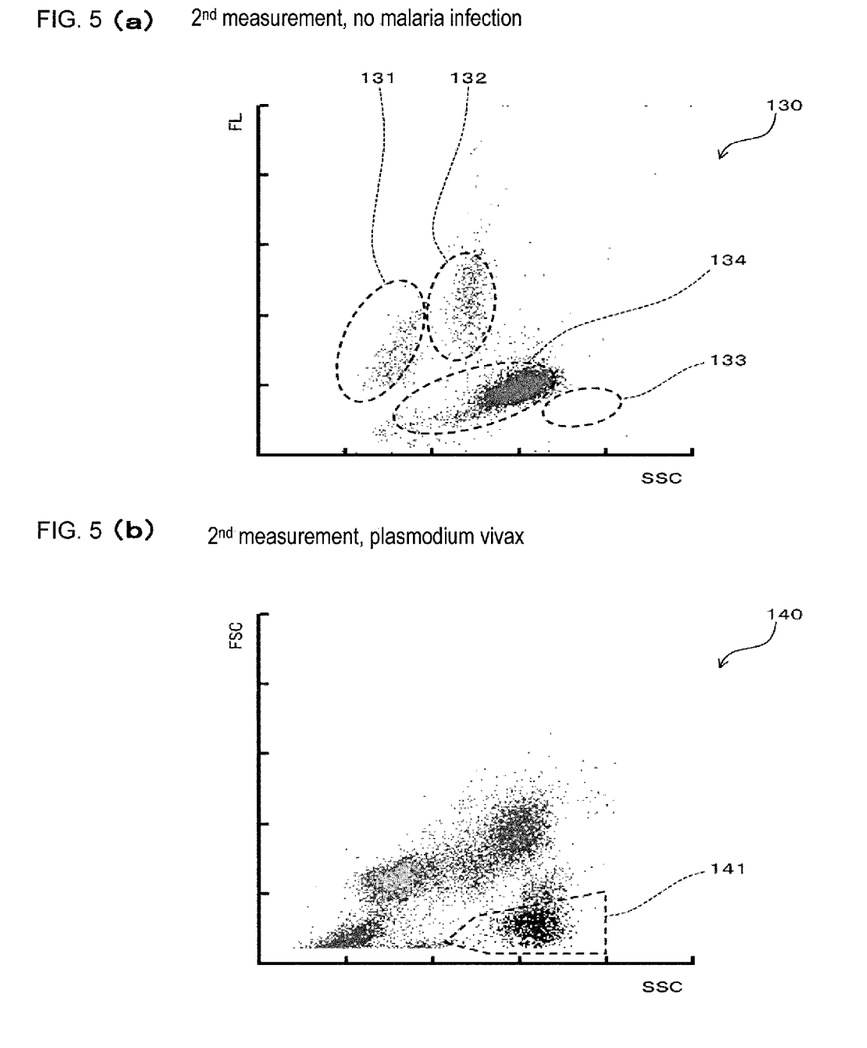

In step S109, the controller 40 prepares a scattergram 130 shown in FIG. 5(a) based on the data obtained in step S108, and sets ranges 131 through 134 on the scattergram 130. The horizontal axis and the vertical axis of the scattergram 110 represent the side scattered light data and the fluorescent light data, respectively. FIG. 5(a) shows the scattergram 130 based on a blood sample 11 collected from a patient who does not have malaria. The ranges 131 through 134 are considered to contain blood cells of lymphocytes, monocytes, eosinophils, and combined neutrophils, and basophils, respectively. The controller 40 classifies the points contained in each range as blood cells corresponding to each of the ranges. In step S110, the controller 40 counts the number of particles contained in ranges 131 through 134, and obtains the number of lymphocytes, monocytes, eosinophils, and combined neutrophils and basophils.

In step S111, the controller 40 prepares a scattergram 140 shown in FIG. 5(b) based on the data obtained in step S108, and sets a range 141 on the scattergram 140. The horizontal axis and the vertical axis of the scattergram 140 represent the side scattered light data and the forward scattered light data, respectively. FIG. 5(b) shows the scattergram 120 based on a blood sample 11 collected from a patient infected with plasmodium vivax malaria.

In this case, the other malaria parasites also can be classified based on the data obtained by the second measurement used to classify white blood cells, although plasmodium falciparum parasites cannot be classified. Range 141 is a range that is considered to contain other malaria parasites. In step S112, the controller 40 counts the number of particles contained in range 121, and obtains the number of other malaria parasites.

In step S113, the controller 40 then determines whether the number of malaria parasites obtained in step S106 is equal to or greater than a predetermined number, and whether the number of malaria parasite obtained in step S112 is equal to or greater than a predetermined number. When the controller 40 determines YES in step S113, there is a possibility of the presence of other malaria parasites in the blood sample 11 and the determination is positive for other malaria parasites in step S114. When the controller 40 determines NO in step S113, there is no possibility of the presence of other malaria parasites in the blood sample 11 and the determination is negative for other malaria parasites in step S115. Thus, the processes related to the first measurement and the second measurement end.

Note that the determination of other malaria parasite in step S113 may be accomplished based on only the number of malaria parasites obtained based on the first measurement, or may be based on only the number of malaria parasites obtained based on the second measurement.

Figure 6:
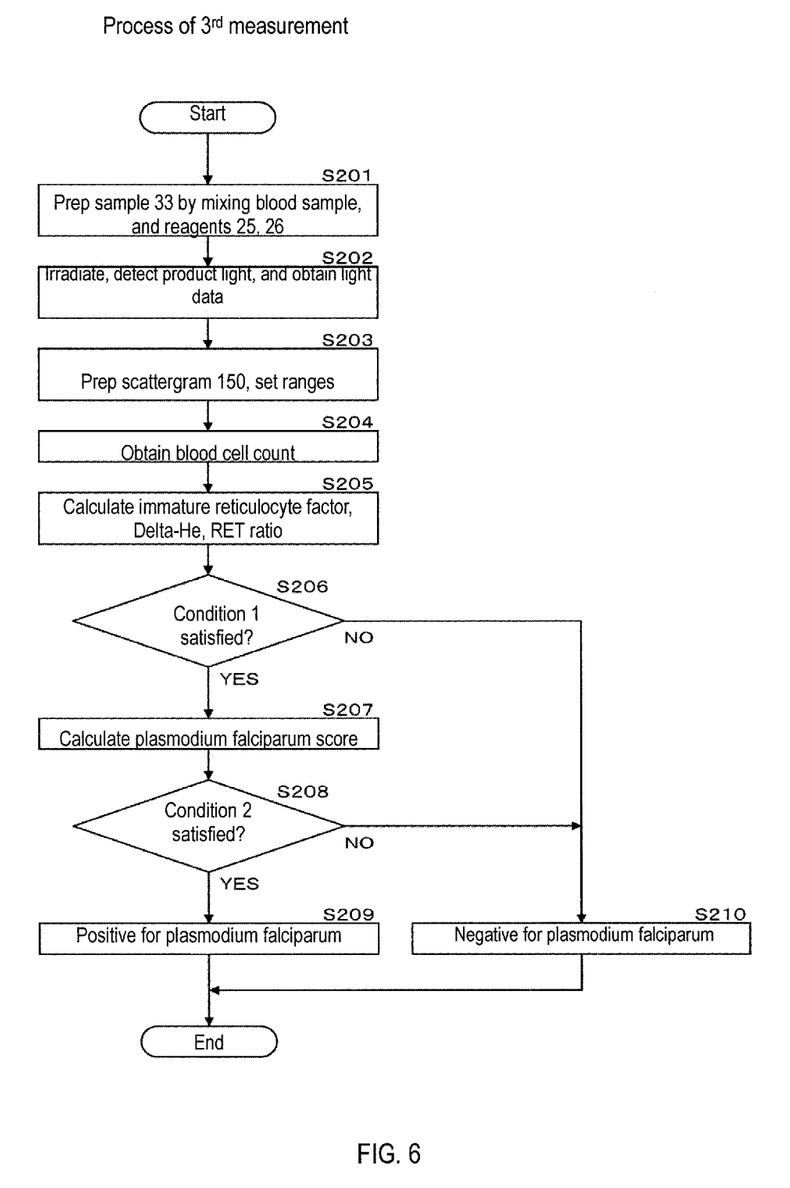
FIG. 6 is a flow chart showing the process related to a third measurement of the embodiment.

As shown in FIG. 6, in step S201 the sample preparing unit 20 prepares the measurement sample 33 by mixing the blood sample 11 and reagents 25 and 26. The red blood cells are not lysed in the preparation of measurement sample 33. When malaria parasites are present in the red blood cells, the malaria parasites are stained by the reagent 26. The detecting unit 30 flows the measurement sample 33 through the flow cell 311. In step S202, the detecting unit 30 obtains each of the light data similar to step S102.

Figure 7:
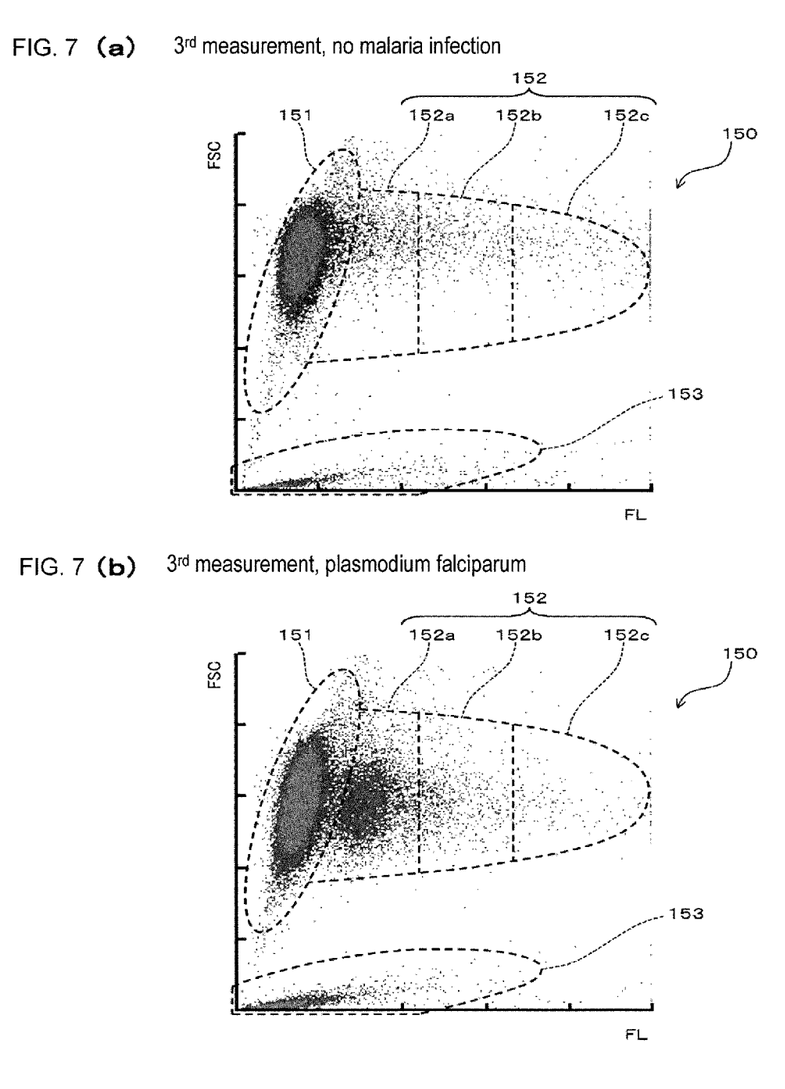

In step S203, the controller 40 prepares a scattergram 150 shown in FIG. 7(a) based on the data obtained in step S202, and sets ranges 151, 152a, 152b, 152c, and 153 on the scattergram 150. The horizontal axis and the vertical axis of the scattergram 150 represent the fluorescent light data and the forward scattered light data, respectively. FIG. 7(a) shows the scattergram 150 based on a blood sample 11 collected from a patient who does not have malaria.

The ranges 151, 152, and 153 are ranges which contain mature red blood cells, reticulocytes, and platelets, respectively. The ranges 152a, 152b, 152c of the ranges 152 are respectively the range of low fluorescence intensity, range of intermediate fluorescence intensity, and range of high fluorescence intensity. The range 152a is considered to contain low fluorescence reticulocytes, that is, reticulocytes which have low fluorescence intensity. The range 152b is considered to contain mid fluorescence reticulocytes, that is, reticulocytes which have intermediate fluorescence intensity. The range 152s is considered to contain high fluorescence reticulocytes, that is, reticulocytes which have high fluorescence intensity. The controller 40 classifies the points contained in each range as blood cells corresponding to each of the ranges.

In step S204, the controller 40 counts the number of particles contained in ranges 151, 152, 152a, 152b, 152c, and 153, and respectively obtains the number of mature red blood cells, number of reticulocytes, number of low fluorescence reticulocytes, number of mid fluorescence reticulocytes, number of high fluorescence reticulocytes, and number of platelets.

In this case the red blood cells containing ring-shaped bodies of plasmodium falciparum parasites were distributed across the boundary between range 151 which is considered the range in which mature red blood cells are distributed, and range 152 which is considered the range in which reticulocytes are distributed. When red blood cells containing plasmodium falciparum parasites are distributed in range 152, the distribution condition of blood cells in range 152 changes from the normal distribution condition, as shown in FIG. 7(b). FIG. 7(b) shows the scattergram 150 based on a blood sample 11 collected from a patient infected with plasmodium falciparum malaria. In this case the controller 40 determines the possibility of the presence of plasmodium falciparum parasites in the blood sample 11 by determining the distribution condition of blood cells in range 152 according to Conditions 1 and 2 which are described later.

In step S205 the controller 40 calculates the immature reticulocyte fraction, Delta-He, and RET ratio by the calculation formula below.

Immature reticulocyte fraction={(mid fluorescence reticulocyte count+high fluorescence reticulocyte count)/reticulocyte count}×100

Delta-He=(RET-He)−(RBC-He)

RET ratio=reticulocyte count/(immature reticulocyte fraction×1000)

The RET-He is the amount of hemoglobin contained in reticulocytes, RBC-He is the amount of hemoglobin contained in mature red blood cells. RET-He is calculated by the following calculation formula using constants C11 and C12 when the average value of the forward scattered light data of particles considered to be reticulocytes contained in range 152 is designated RET-Y.

RET-He=$C11 \times \exp(C12 \times \text{RET-}Y)$

RBC-He is calculated by the following calculation formula using constants C13 and C14 when the average value of the forward scattered light data of particles considered to be mature red blood cells contained in range 151 is designated RBC-Y.

$$RBC\text{-}He = C13 \times \exp(C14 \times RBC\text{-}Y)$$

In step S206, the controller 40 determines whether Condition 1 is satisfied. When Conditions (1) through (4) below are completely satisfied, Condition 1 is satisfied. Sh1 through Sh4 are preset threshold values.

Condition 1
(1) Number of reticulocytes is equal to or greater than Sh1
(2) Immature reticulocyte fraction is equal to or less than Sh2
(3) Delta-He is equal to or less than Sh3
(4) RET ratio is equal to or less than Sh4

The red blood cells containing *plasmodium falciparum* parasite are distributed so as to straddle the boundary between ranges 151 and 152, as mentioned above. Accordingly, Condition (1) is more easily satisfied when the red blood cells containing *plasmodium falciparum* parasite increase, since the number of red blood cells contained in range 152 increases. Further, Conditions (2) and (4) also are easily satisfied when the red blood cells containing *plasmodium falciparum* parasite increase, since the blood cells contained in the range 152 will be disproportionately distributed to the range 152*a* side. In other words, in conditions (2) and (4) it is determined whether there is a high percentage of blood cells contained in the low fluorescence intensity range in range 152 corresponding to reticulocytes.

In this case, the centroid position based on forward scattered light data of particles considered reticulocytes contained in range 152 is designated the first centroid position, and the centroid position based on the forward scattered light data of particles considered mature red blood cells contained in range 151 is designated the second centroid position. The first centroid position is the average value of the forward scattered light data of particles considered reticulocytes contained in range 152, that is, RET-Y; the second centroid position is the average value of the forward scattered light data of particles considered mature red blood cells contained in range 151, that is, RBC-Y. RET-He and RBC-He are calculated using RET-Y and RBC-Y, respectively. RET-He and RBC-He are values which respectively reflect the first centroid position and the second centroid position.

Accordingly, the values reflecting the first centroid position and the second centroid position can be obtained in the manner described below. That is, RET-Y is obtained by the average value of the forward scattered light data of particles considered reticulocytes contained in range 152, and RBC-Y is obtained by the average value of the forward scattered light data of particles considered mature red blood cells contained in range 151. Then, a value reflecting the first centroid position is obtained by $C11 \times \exp(C12 \times RET\text{-}Y)$, and a value reflecting the second centroid position is obtained by $C13 \times \exp(C14 \times RBC\text{-}Y)$.

Red blood cells containing *plasmodium falciparum* parasite appears somewhat lower than reticulocytes on the scattergram 150. That is, the forward scattered light data of red blood cells containing *plasmodium falciparum* parasites are small compared to the forward scattered light data of normal reticulocytes which do not contain malaria parasites. When *plasmodium falciparum* parasites are present in the blood sample 11, the first centroid position is lower. Lowering of the first centroid position can be determined by reducing the differential between the first centroid position and the second centroid position. As described above, RET-He and RBC-He are values which respectively reflect the first centroid position and the second centroid position. Accordingly, the reduction of the differential between the first centroid position and the second centroid position can be determined by the differential of RET-He and RBC-He, that is, Delta-He. Hence, Delta-He becomes smaller as the red blood cell containing *plasmodium falciparum* parasites increase, and Condition (3) is easily satisfied.

Note that in condition (3) whether the differential of the first centroid position and the second centroid position is less than a predetermined threshold can be determined using other values reflecting the first centroid position and the second centroid position. For example, a value reflecting the first centroid position may be obtained by RET-Y, and a value reflecting the second centroid position may be obtained by RBC-Y. Then, whether the differential between RET-Y and RBC-Y is less than a predetermined threshold can be determined in Condition (3).

In this way the conditions (1) through (4) are respectively and easily satisfied when *plasmodium falciparum* parasites are present in the blood sample 11 and the red blood cells containing the *plasmodium falciparum* parasite increase. Accordingly, when Conditions (1) through (4) are all satisfied, that is, when Condition 1 is satisfied, there is a high possibility of the presence of *plasmodium falciparum* parasites in the blood sample 11. The process continues to step S207 when the controller 40 determines YES in step S206, and the process advances to step S210 when the controller 40 determines NO in step S206.

In step S207, the controller 40 calculates the *plasmodium falciparum* score. The *plasmodium falciparum* score is calculated by the following calculation formula using constants C21 through C24.

$$\text{Score} = (\text{RET ratio}) \times C21 - \text{platelet count} \times C22 - (\text{Delta-He}) \times C23 + C24$$

Constants C21 through C24 are preset to allow determination of the possibility of the presence of *plasmodium falciparum* parasite in blood sample 11 by comparing the *plasmodium falciparum* score and a predetermined reference value in Condition (5) to be described later. In this case the reference value is set at 100.

In step S208, the controller 40 determines whether Condition 2 is satisfied. When Condition (5) shown below is satisfied, Condition 2 is satisfied.

Condition 2
(5) *Plasmodium falciparum* score is greater than 100.

When red blood cells containing *plasmodium falciparum* increase, the RET ratio increases and the Delta-He decreases as mentioned above. When *plasmodium falciparum* infects a patient, there is a reduction in the number of platelets in the blood sample 11. Accordingly, when a patient is infected by *plasmodium falciparum* and *plasmodium falciparum* is present in the blood sample 11, condition (5) is easily satisfied, and hence Condition 2 is easily satisfied. When Condition 2 is satisfied, there is therefore a high possibility of the presence of *plasmodium falciparum* in the blood sample 11. The process continues to step S209 when the controller 40 determines YES in step S208, and the process advances to step S210 when the controller 40 determines NO in step S208.

When the controller 40 determines YES in steps S206 and S208, that is when Conditions 1 and 2 are satisfied, there is a possibility of the presence of *plasmodium falciparum* in the blood sample 11 in step S209, and the controller 40 makes a positive determination for *plasmodium falciparum*. However, when the controller 40 determines NO in either step S206 or S208, that is when either Condition 1 or 2 is not satisfied, there is no possibility of the presence of *plasmodium falciparum* in the blood sample 11 in step S209, and the controller 40 makes a negative determination for *plasmodium falciparum*. Thus, the process related to the third measurement ends.

Conditions 1 and 2 are determined by the change in the blood cell distribution condition in range 152 from the normal distribution condition based on blood cell distribution condition in range 152. Accordingly, either step S206 or S208 may be omitted from the process related to the third measurement. That is, *plasmodium falciparum* may be determined to be positive when Condition 1 is satisfied, and *plasmodium falciparum* may be determined to be positive when Condition 2 is satisfied.

According to the third measurement, particles are classified as mature red blood cells, reticulocytes, and platelets based on the detected scattered light data and fluorescent light data of the particles. The possibility of the presence of *plasmodium falciparum* parasite in the blood sample 11 is determined by determining the blood cell distribution condition in range 152 which is considered to be the distribution of reticulocytes via Conditions 1 and 2. Therefore, the classification of red blood cells and the determination of *plasmodium falciparum* malaria can be performed simultaneously.

According to the third measurement, the possibility of the presence of *plasmodium falciparum* parasite can be determined by the processes of steps S205 through S210 of FIG. 6 alone. Accordingly, the possibility of the presence of *plasmodium falciparum* parasite can be determined by just including the program for executing the processes of steps S205 through S210 in the program 51 of the apparatus even when the possibility of the presence of *plasmodium falciparum* parasite cannot be determined in the apparatus performing the third measurement. In this case, the program for executing the processes of steps S205 through S210 is stored in the storage unit 50 from outside the apparatus through the communication unit 80 and the reader unit 90.

Note that when other malaria parasites are present in the blood sample 11, the red blood cells containing the other malaria parasites are positioned in the vicinity of the top end or the vicinity of the right end of the scattergram 150. Therefore, it is difficult to accurately determine the possibility of the presence of other malaria parasites in the blood sample 11 by the process related to the third measurement. However, the possibility of the presence of other malaria parasites in the blood sample 11 can be determined by processes related to the first measurement and the second measurement shown in FIG. 3. Therefore, the possibility of the presence of all malaria parasites in the blood sample 11 can be determined by the processes of the first through third measurements.

The display process is executed when the process related to the first measurement and the second measurement, and the process related to the third measurement end.

Figure 8:
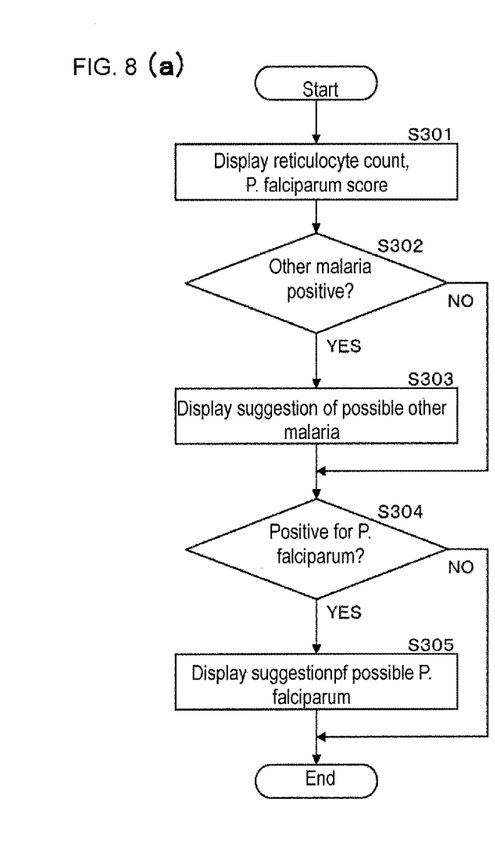

As shown in FIG. 8(*a*), in step S301 the controller 40 displays the screen 200 which includes the reticulocyte count and the *plasmodium falciparum* score on the display unit 70. FIGS. 8(*b*) and (*c*) respectively show a screen example of the positive determination of other malaria and positive determination of *plasmodium falciparum*. In FIGS. 8(*b*) and (*c*), the reticulocyte count obtained in step S204 of FIG. 6 is arranged at a suitable position in region 210. The *plasmodium falciparum* score and a bar to make the *plasmodium falciparum* score visually comprehensible are shown in region 220.

In step S302, the controller 40 makes a positive determination for other malaria based on the determination performed in the process related to the first measurement and the second measurement. When other malaria is positive, the controller 40 displays a suggestion of the possibility of the presence of other malaria in the blood sample 11 in step S303. Specifically, the message [*Plasmodium vivax, plasmodium ovale, plasmodium malariae*?] is displayed in region 230, as shown in FIG. 8(*c*).

In step S304, the controller 40 makes a positive determination of *plasmodium falciparum* based on the determination performed in the process related to the third measurement. When *plasmodium falciparum* is positive, the controller 40 displays a suggestion of the possibility of the presence of *plasmodium falciparum* in the blood sample 11 in step S305. Specifically, the message [*Plasmodium falciparum*?] is displayed in region 230, as shown in FIG. 8(*c*).

According to the display process, the operator is informed of whether there is a possibility of the presence of *plasmodium falciparum* in the blood sample 11 collected from a patient by viewing the content of the display in regions 220 and 230.

Then, the possibility of the presence of *plasmodium falciparum* parasites when the determination is made by the process related to the first measurement and the second measurement, and when the determination is made by the process related to the third measurement are compared while showing the actual measurement results. In either case the determination is made for the same blood sample group. The number of blood samples used as determination subjects was 99. The number of blood samples visually determined to be positive and negative were 23 and 76, respectively.

Sensitivity is the ratio of the number of blood samples determined to be positive by determination result relative to the number of blood samples determined to be positive visually. Specificity is the ratio of the number of blood samples determined to be positive by determination result relative to the number of blood samples determined to be negative visually. PPV (positive predictive value) is the ratio of the number of blood samples determined to be positive visually relative to the number of blood samples determined to be positive by determination result. NPV (negative predictive value) is the ratio of the number of blood samples determined to be negative visually relative to the number of blood samples determined to be negative by determination result.

Figure 9A:
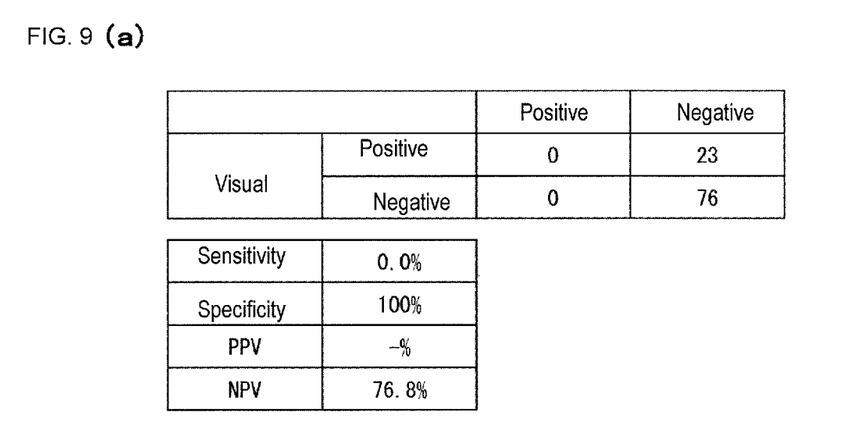
FIG. 9(a) shows the results when the possibility of the presence of *plasmodium falciparum* parasites is determined by the process related to the first measurement and the second measurement.

As shown in FIG. 9(*a*), according to the process related to the first measurement and the second measurement, 23 individual blood samples determined to be positive visually and 76 individual blood samples determined to the negative visually were all determined to be negative. Hence, the NPV was 76.8%.

Figure 9B:
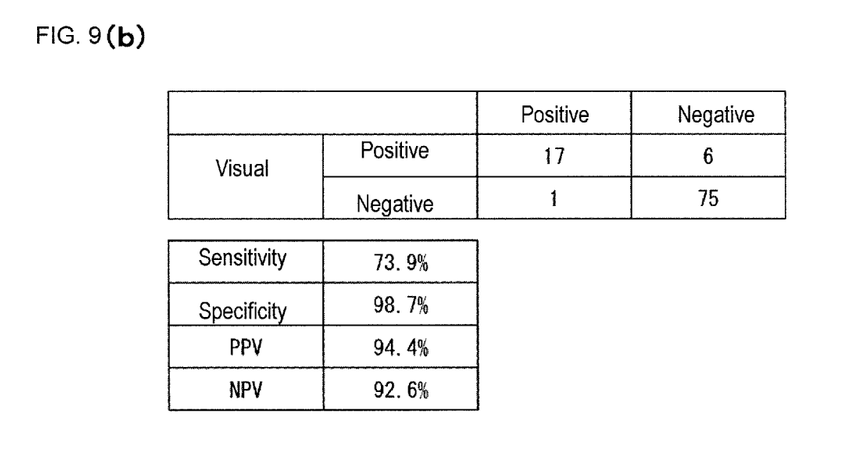
FIG. 9(b) shows the results when the possibility of the presence of *plasmodium falciparum* parasites is determined by the process related to the third measurement.

On the other hand, according to the process related to the third measurement, among the 23 blood samples which were determined to be positive visually, 17 blood samples determined to be positive and 6 blood samples were determined to be negative, as shown in FIG. 9(*b*). Among the 76 individual blood samples which were determined to be negative visually, 1 blood sample was determined to be positive and 75 blood samples were determined to be negative. Thus, the NPV improved from 76.8% to 92.6%, and the PPV was 94.4%.

As can be understood from the above measurement results, the possibility of the presence of *plasmodium falciparum* parasite in blood sample 11 can be determined with higher accuracy according to the process of the third measurement, compared to the process related to the first measurement and the second measurement.

What is claimed is:

1. A blood analyzer, comprising:
a sample preparing apparatus configured to mix a fluorescent dye and a blood sample to prepare a measurement sample without lysing red blood cells to produce a difference in fluorescence intensity between mature red blood cells and reticulocytes in the measurement sample;
a detecting apparatus comprising a light source and a plurality of photodetectors, wherein the plurality of photodetectors respectively detect scattered light and fluorescent light produced from the measurement sample after being irradiated with light from the light source on the unlysed blood cells in the measurement sample, wherein the plurality of photodetectors respectively outputting fluorescence data related to the fluorescent light and scattered light data related to the scattered light for each unlysed blood cell in the measurement sample; and
a hardware controller comprising a processor which executes a program stored in—a non-transitory memory—to:
output scattergram data to display a plot, wherein the plot having an intensity of the fluorescence data related to the fluorescent light on one axis and an intensity of the scattered light data related to the scattered light on another axis, wherein a range of the intensity of the detected fluorescence data is partitioned into a mature red blood cell distribution range and a reticulocyte distribution range, wherein the reticulocyte distribution range is further partitioned into a low fluorescence intensity range, a mid fluorescence intensity range and a high fluorescence intensity range;
obtain from the scattergram data, a proportion of the unlysed blood cells included in the low fluorescence intensity range in the reticulocyte distribution range;
obtain a first value reflecting a first centroid position based on the scattered light data in the reticulocyte distribution range;
obtain a second value reflecting a second centroid position based on the scattered light data in the mature red blood cell distribution range; and
determine the presence of *plasmodium falciparum* parasites in the unlysed blood sample based on the proportion of the unlysed blood cells included in the low fluorescence intensity range in the reticulocyte distribution range and a difference between the first value reflecting the first centroid position and the second value reflecting the second centroid position.

2. The blood analyzer of claim 1, wherein the hardware controller is further programmed to classify blood cells in the measurement sample are classified as the mature red blood cells, reticulocytes, and platelets based on the scattered light data and the fluorescent light data.

3. The blood analyzer of claim 1, wherein the hardware controller is further programmed to determine the presence of *plasmodium falciparum* parasites based on the number of blood cells included in a platelet distribution range based on the scattered light data and the fluorescent light data.

4. The blood analyzer of claim 1, wherein the hardware controller is further programmed to determine the presence of *plasmodium falciparum* parasites based on the number of blood cells included in the reticulocyte distribution range.

5. The blood analyzer of claim 1, further comprising an output part, wherein the hardware controller is configured to display information related to the possibility of the presence of *plasmodium falciparum* parasites on the output part.

* * * * *